United States Patent
Eck et al.

(10) Patent No.: US 8,090,427 B2
(45) Date of Patent: Jan. 3, 2012

(54) METHODS FOR ULTRASOUND VISUALIZATION OF A VESSEL WITH LOCATION AND CYCLE INFORMATION

(75) Inventors: Kai Eck, Aachen (DE); Barbara Martin-Leung, Aachen (DE); Jorg Bredno, Aachen (DE); Jurgen Weese, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/605,508

(22) Filed: Oct. 26, 2009

(65) Prior Publication Data

US 2010/0049034 A1 Feb. 25, 2010

Related U.S. Application Data

(63) Continuation of application No. 10/570,235, filed as application No. PCT/IB2004/051525 on Aug. 23, 2004, now abandoned.

(30) Foreign Application Priority Data

Sep. 4, 2003 (EP) .................................. 03102691

(51) Int. Cl.
*A61B 5/05* (2006.01)
*A61B 8/00* (2006.01)

(52) U.S. Cl. .......................... 600/425; 600/462; 600/466

(58) Field of Classification Search .................. 600/424, 600/425, 427, 437, 467, 440; 382/128, 132, 382/285, 294–296
See application file for complete search history.

(56) References Cited

U.S. PATENT DOCUMENTS

| | | | |
|---|---|---|---|
| 5,345,938 A | 9/1994 | Nishiki et al. | |
| 6,148,095 A | 11/2000 | Prause et al. | |
| 6,351,513 B1 | 2/2002 | Bani-Hashemi et al. | |
| 6,389,104 B1 | 5/2002 | Bani-Hashemi et al. | |
| 6,473,635 B1 | 10/2002 | Rasche | |
| 6,484,049 B1 | 11/2002 | Seeley et al. | |
| 2002/0049375 A1 | 4/2002 | Strommer et al. | |
| 2002/0077546 A1 | 6/2002 | Aldefeld et al. | |

OTHER PUBLICATIONS

Buzug et al: "Motion Dettection and Motion Compensation for Digital Subtraction Angiography Image Enhancement": Philips Journal of Research, Elsevier, Amsterdam, NL., vol. 51, No. 2, 1998, pp. 203-229, XP004126960.
ISR of International Publication No. PCT/IB2004/051525 Contained in International Publication No. WO2005/024729.
Written Opinion of International Publication PCT/IB2004/051525.

*Primary Examiner* — Parikha Mehta

(57) ABSTRACT

Methods for displaying a vessel with the aid of intravascular ultrasound images and current location and cycle information provided by detectors and sensors. A sequence of intravascular ultrasound images are stored and indexed-by location and by heartbeat and breathing phase. During a subsequent medical intervention, ultrasound images that correspond to the current phase and location of an object of interest such as a catheter can be selected and displayed on a monitor in real time along with an x-ray image of the vessel, the display showing the geometric position of the ultrasound images with reference to the x-ray image.

7 Claims, 1 Drawing Sheet

Figure 1:
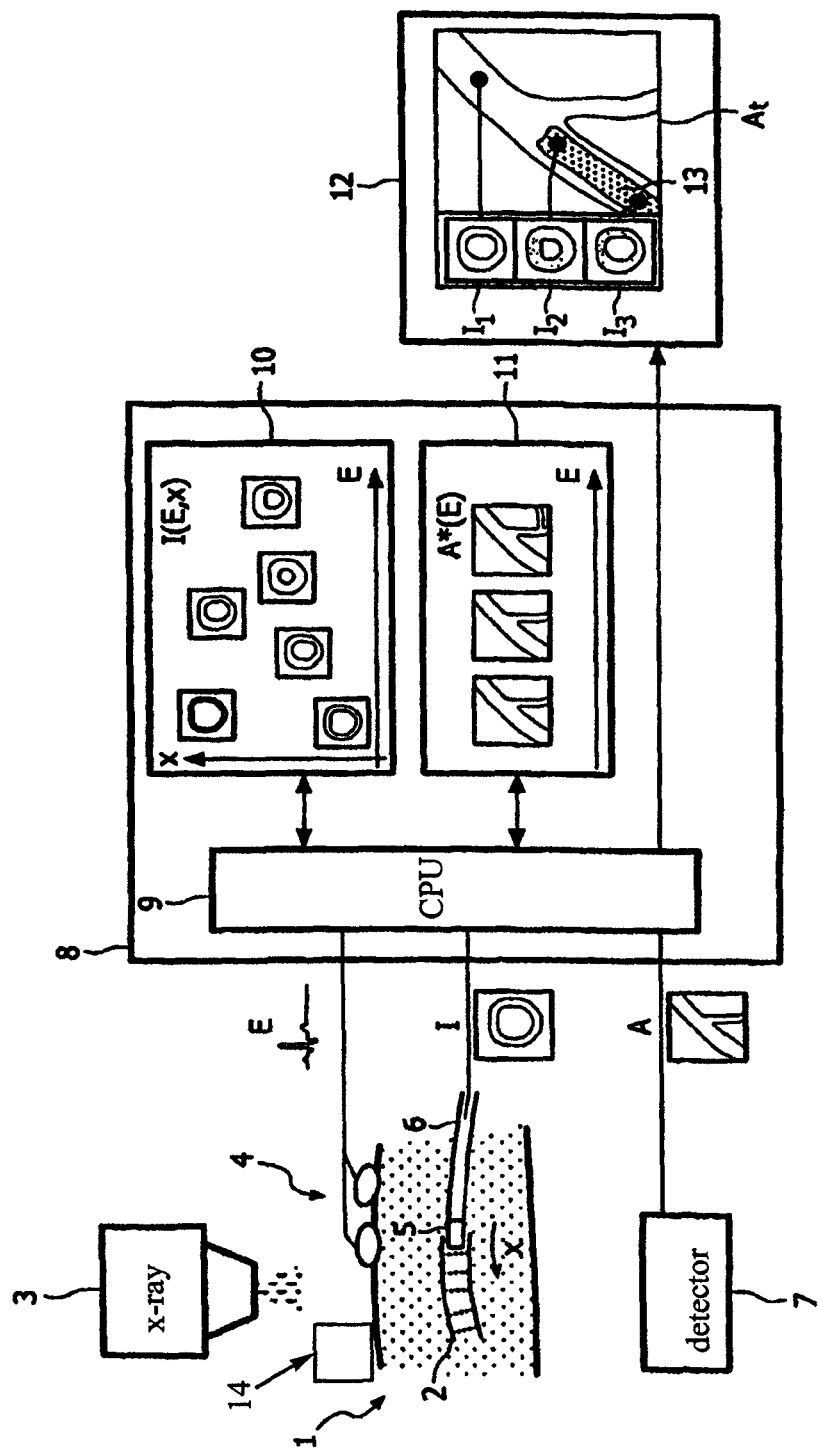

METHODS FOR ULTRASOUND VISUALIZATION OF A VESSEL WITH LOCATION AND CYCLE INFORMATION

This application is a continuation of prior U.S. application No. 10/570,235, filed Feb. 28, 2006, now abandoned, which is the National Stage Entry of PCT International Application PCT/IB04/51525, filed Aug. 23, 2004.

The invention relates to a device and a method for displaying a vessel with the aid of ultrasound images, the vessel being subject to a cyclic intrinsic movement.

In catheter examinations of the heart, a number of angiographic X-ray images of the heart are usually generated from various directions, a contrast agent typically being injected during the recording. The angiograms of the vascular system that are thus obtained may than be of assistance, for example, in locating the site of a lesion that is to be treated, or else they may be used as (static) road maps for navigating a catheter during a subsequent medical intervention.

Moreover, so-called intravascular ultrasound probes (IVUS probes) are used, which can be guided for example by means of a catheter through a vessel and generate ultrasound section images transversely to the vessel axis. Ultrasound images are often generated in a so-called pullback sequence using an IVUS probe. In this case, the IVUS probe is pulled back through the vessel at a defined speed while at the same time recording a series of ultrasound images. The IVUS images provide useful additional information about the vessel or a vessel lesion, for example the length of a vessel section affected by a disease, the minimum/maximum thickness of a vessel, the type of a deposit and the like.

U.S. Pat. No. 6,148,095 discloses a method of reconstructing three-dimensionally winding vessels such as, for example, the coronary vessels, in which firstly the three-dimensional course of the vessel is reconstructed from biplanar angiographs, and this is then combined with the two-dimensional section images of an IVUS pullback sequence. Although good reconstruction of the three-dimensional course of the vessel is possible by means of the method, the result is a static representation of the vascular tree, in which intrinsic movements and deformations on account of the heartbeat and/or breathing cannot be seen. When navigating a catheter with an intervention device such as, for example, a stent or a balloon toward a lesion during a medical intervention, the treating physician therefore has to correlate the current fluoroscopic images of the catheter with the static three-dimensional vessel model in order to be able to use the information contained in the IVUS images.

Against this background, it is an object of the present invention to provide means of displaying a vessel which allow more convenient use of information from intravascular ultrasound images, this being continually adapted to an ongoing medical intervention.

This object is achieved according to a first aspect of the invention by a device having the features of claim 1, according to a second aspect of the invention by a device having the features of claim 2, and also by methods having the features of claims 10 and 11. Advantageous refinements are given in the dependent claims.

According to a first aspect of the invention, the device, which is used to display a vessel or a section of a vascular system, comprises the following components:

a) a (data) memory in which a sequence of intravascular ultrasound images is stored, the ultrasound images being indexed by the respective locations (x) of their recording in the vessel. Said ultrasound images may have been generated, for example, with the aid of an intravascular ultrasound probe. In particular, the images may come from an IVUS pullback sequence, wherein as the IVUS probe is being pulled back, the respective stopping location of the IVUS probe in the vessel is determined in parallel by means of further imaging. The latter may moreover be estimated from existing images of the vascular system (angiographs).

b) a data input for information which describes (at least) a current location in the vessel. By way of example, a pointer (mouse, etc.) could be connected to this input, by means of which pointer a user indicates, on a road map, a current location of interest to him in the vessel, or else a locating device could be connected to said input, which locating device detects, for example by means of magnetic fields, the current stopping location of an intervention device on a catheter. Other examples will be described within the context of the developments of the invention.

c) a display unit such as, for example, a monitor for displaying images of the vessel.

The device comprising the described components is furthermore designed to select from said memory at least one ultrasound image and to display it on the display unit, wherein the ultrasound image corresponds to the current location in the vessel indicated at the data input. By way of example, an ultrasound image whose associated recording location is identical to the current location or is no more than a predefined distance from the latter may be selected from the memory. The selection function may be implemented in the device for example by means of a suitably programmed microprocessor.

According to a second aspect, the invention comprises a device for displaying a vessel or a section of a vascular system which is subject to a cyclic intrinsic movement. The most important typical causes of such an intrinsic movement are the heartbeat and breathing. The most important typical causes of a change in the vessel cross section is pathological constriction. The cyclic intrinsic movement is to be characterized by a (single-component or multicomponent) parameter. For the heartbeat, this parameter is for example the electrical heartbeat phase that can be quantitatively described by the electrocardiogram (ECG). The device comprises the following components:

a) a (data) memory in which a sequence of intravascular ultrasound images is stored, the ultrasound images being indexed by the respective values of the parameter of the intrinsic movement belonging to the recording time. Said ultrasound images may have been generated, for example, with the aid of an intravascular ultrasound probe. In particular, the images may come from an IVUS pullback sequence, wherein as the IVUS probe is being pulled back, the parameter of the intrinsic movement (for example the ECG) is recorded in parallel, as is preferably also the respective stopping location of the IVUS probe in the vessel, using methods of the type mentioned above. The latter may moreover be estimated from existing images of the vascular system (angiographs).

b) a data input for the current value of the parameter of the intrinsic movement.

c) a display unit such as, for example, a monitor for displaying images of the vessel.

The device comprising the described components is furthermore designed to select from said memory at least one ultrasound image and to display it on the display unit, wherein the selected ultrasound image corresponds to the current value of the parameter of the intrinsic movement at the data input. By way of example, an ultrasound image whose associated ECG phase is identical to the current ECG phase or deviates from the latter by no more than a predefined amount may be selected from the memory. The selection function may be implemented in the device for example by means of a suitably programmed microprocessor. The device may moreover also have the features of a device according to the first aspect of the invention, that is to say an additional indexing of the ultrasound images by their recording location, a data input for a current location and also a selection function that is additionally based on the location. On account of the analog structure of the devices and their ability to be combined, special refinements of the invention are hereinbelow described in parallel for the "device according to the first and/or second aspect of the invention".

The described devices according to the first and/or second aspect of the invention allow, in real time during a medical intervention, optimal use of information contained in IVUS images of a vessel or vessel lesion. This is made possible in that the device determines and displays on the display unit the IVUS image(s) corresponding to a current location in the vessel and/or to the current phase of the cyclic intrinsic movement. The physician therefore need not be satisfied with a possibly misleading static display of IVUS images, but rather sees at all times the images corresponding to the actual state. This makes it much easier for him to navigate a catheter to the desired target position such as, for example, a stenosis.

As has already been mentioned, the causes of the cyclic intrinsic movement of vessels are primarily the heartbeat and breathing. The device according to the first and/or second aspect of the invention therefore preferably comprises an electrocardiograph for recording a (electrical) parameter that characterizes the heart phase and/or a breathing sensor (14) for recording a parameter that characterizes the breathing phase.

The device according to the first and/or second aspect of the invention furthermore preferably comprises an intravascular ultrasound probe (IVUS probe), by means of which the ultrasound images stored in said memory can be generated. As mentioned in the introduction, such IVUS images contain useful additional information for assessing the condition of a vessel.

The device according to the first and/or second aspect of the invention may furthermore comprise an X-ray device for generating X-ray projection images of the vessel. The X-ray device may in particular be coupled to a data input of the device in order to provide a current image of the vessel in the form of an X-ray projection image. Moreover, the X-ray projections may also be used during generation of a (pullback) sequence of IVUS images, in order to determine the respective stopping location of the IVUS probe.

In another development, the device according to the first and/or second aspect of the invention comprises a device for injecting contrast agent into the vessel. By means of contrast agent injections it is possible to considerably improve the representation of the vessel on (X-ray) images. In particular, angiograms can be produced using a contrast agent and an X-ray device.

Furthermore, the device according to the first and/or second aspect of the invention may comprise a further memory in which angiograms of the vessel are stored, these being indexed with the respective values of the parameter of the cyclic intrinsic movement belonging to their recording time according to the second aspect of the invention. For each of the stored angiograms it is thus known from which phase of the cyclic intrinsic movement it comes. The device is in this case furthermore designed to select from said further memory and display on the display unit at least one angiogram corresponding to the current value of the parameter of the intrinsic movement. The angiograms, which clearly show the course of the vessel, are thus displayed on the display unit in real time in a manner corresponding to the actual state of the intrinsic movement (for example heartbeat phase or breathing phase). The ultrasound images and the angiograms are preferably stored in the same physical memory at different storage locations.

In another development of the device according to the first aspect of the invention, said device has a data input for data of a current image of the vessel. This current image may be, for example, an X-ray image or an NMR image of the vessel. Furthermore, the device is designed to determine from a current image of the vessel the position of an object of interest (e.g. a specific anatomical structure or a catheter in the vessel) and use it as "current location" to select a corresponding ultrasound image from the memory. In other words, of the stored ultrasound images, only those which show the vessel in the region of the object are displayed on the display unit. The physician thus obtains a display of ultrasound images that is updated in real time and corresponds to the position of an object of interest, so that he can make optimal use of the information contained therein. Furthermore, the current image present in each case at the data input is preferably also displayed on the display unit together with the intravascular ultrasound images, and this allows the physician to observe a medical intervention in an optimal manner.

When, in the abovementioned case, the intravascular ultrasound images are indexed by the location of their recording, the device according to the first and/or second aspect of the invention may furthermore be designed to display an (any) image of the vessel on the display unit and to show with reference to this image the geometric position of an ultrasound image that is likewise displayed on the display unit. The image of the vessel may for example be a current image or a stored angiogram of the vessel. Since, in respect of each ultrasound image, it is known at which position of the vessel it was generated, this position of the ultrasound image can be marked, for example by means of an arrow or a cross, on the image of the vessel that is displayed. The user can then see at a glance to which location a displayed ultrasound image belongs.

The invention furthermore relates to a method of displaying a vessel, said method comprising the following steps:
 a) generating a sequence of intravascular ultrasound images while at the same time recording the associated locations in the vessel,
 b) detecting a current location in the vessel and optionally generating a current image of the vessel,
 c) selecting at least one ultrasound image corresponding to the current location,
 d) displaying the selected ultrasound image, optionally together with a current image or a stored image corresponding thereto.

The invention moreover also relates to a method of displaying a vessel which is subject to a cyclic intrinsic movement that can be characterized by a parameter. The method may in particular be combined with a method of the type mentioned above and comprises the following steps:
 a) generating a sequence of intravascular ultrasound images while at the same time recording the associated parameters of the intrinsic movement,
 b) determining the current value of the parameter of the intrinsic movement and optionally generating a current image of the vessel,
 c) selecting at least one ultrasound image corresponding to the current value of the parameter of the intrinsic movement, d) displaying the selected ultrasound image, optionally together with the current image or a stored image corresponding thereto.

Said methods in general implement the steps that can be carried out using a device according to the first and/or second aspect of the invention. With regard to a description of the details, advantages and developments of the method, reference is therefore made to the explanations given above.

The invention will be further described with reference to an example of embodiment shown in the drawing to which, however, the invention is not restricted.

The single FIGURE schematically shows the components of a device according to the invention for displaying a vessel.

The left-hand part of the FIGURE shows a vessel (segment) 2 within the body of a patient 1, wherein said vessel may be, for example, a coronary vessel. X-ray projection images A of the vessel 2 may be generated by means of an X-ray radiation source 3 and an X-ray detector 7, and forwarded to a data processing device 8 (workstation, etc.).

Furthermore, an IVUS probe 5 for generating intravascular ultrasound images I is arranged at the tip of a catheter 6. By means of the IVUS probe 5, in particular a so-called pullback sequence (see dashed lines) can be generated when the probe 5 is pulled back through the vessel at a defined speed and in the process generates ultrasound section images I at regular time intervals, said ultrasound section images being transmitted to the data processing device 8. The position of the IVUS probe 5 during an image I generated by the latter, which position can be described by a coordinate x, may be determined in various ways. For instance, by way of example it is possible during the ultrasound recordings for X-ray projections to be produced at the same time, from which the associated position of the IVUS probe 5 can be determined. In order to reduce the X-ray exposure for the patient 1, however, it is also possible for X-ray projections to be generated only at the start and at the end of the IVUS pullback sequence, it being possible for the positions of the intermediate IVUS images to be estimated on account of the defined pullback speed of the probe 5.

Furthermore, an electrocardiograph 4 is also shown in the left-hand part of the FIGURE, by means of which the electrical heart activity E (electrocardiogram) can be recorded and fed to the data processing device 8. The ECG represents a parameter E for characterizing the heartbeat phase, which has a dominating effect on the location and the shape of the vessel 2.

The data processing device 8 comprises a central processor 9 (CPU) which receives the abovementioned information (ECG E, IVUS images I, X-ray projections A) and further processes it. The processor 9 is connected to two memories or memory areas 10 and 11 (RAM, hard disk, etc.) and also to a display unit 12 (monitor).

Stored in the first memory area 10 are the IVUS images I which have been generated in a pullback sequence of the IVUS probe 5. During the pullback sequence, the ECG E was recorded in parallel. Each of the IVUS images stored in the memory area 10 can thus be indexed by the heartbeat phase E at the time they were generated and the location x where they were generated: I=I(E, x). Since an IVUS pullback sequence typically lasts about 30 seconds (and comprises about 10 to 30 ultrasound images per second), about 30 heart cycles and two to four breathing cycles fall within the time of the sequence. The sensory detection of the breathing cycle and the indexing of the ultrasound images I with a corresponding parameter is not shown in the FIGURE for reasons of clarity. However, it is preferably likewise carried out and dealt with in a manner similar to the characterizing by the ECG E.

The second memory area 11 comprises a sequence of angiograms A*. These are X-ray projections of the vessel 2 which have been recorded with administration of contrast agent. By virtue of a parallel recording of the ECG E, the angiograms A* can once again be indexed by the associated heartbeat phase (and in accordance with what has been stated above also by a breathing cycle).

The generation of the ultrasound images I(E,x) of the memory area 10 and where appropriate of the angiograms A*(E) of the memory area 11 takes place in the run-up to a medical intervention. During the actual intervention, e.g. the placing of a stent with the aid of a catheter 13, the catheter must be pushed as precisely as possible up to the actual stenosis with continual X-ray-fluoroscopic observation (but without contrast agent in order to minimize the exposure of the patient). The precise placing of the stent in this case has a decisive effect on the success of the intervention or the risk of subsequent restenosis. In order in this connection to allow the physician to make optimal use of the available information in real time during the intervention, the data processing device 8 is designed, by means of corresponding programs for the processor 9, etc., to carry out the steps explained below.

Firstly, as already mentioned above, the catheter 13 is pushed up to the lesion under continual fluoroscopic observation. On each current fluoroscopic X-ray image $A_t$ provided by the X-ray device 3, 7, the instantaneous stopping location of the catheter 13 is located by the data processing device 8, and the X-ray image $A_t$ is displayed on the display unit 12. By virtue of the electrocardiogram E recorded at the same time, the angiographic image A*(E) that best corresponds to the current fluoroscopic image $A_t$ in terms of the ECG phase can be selected from the memory area 11, and displayed for example on the display unit 12 next to the image $A_t$ or superposed on the latter. Details of such a combination of current fluoroscopic images and static "road maps" are known and therefore do not have to be discussed in any more detail in the present text.

Furthermore, one or more IVUS images I(E,x) are selected from the memory area 10 by the data processing device 8 in a manner corresponding to the ECG phase E of the current image $A_t$. In the example shown, three IVUS images $I_1, I_2, I_3$ have been determined in this way and displayed on the display unit 12 next to the picture of the current image $A_t$. The choice of IVUS images $I_1, I_2, I_3$ corresponding to the heartbeat phase of the current image $A_t$ ensures that the physician is shown on the monitor 12 at all times X-ray information and intravascular ultrasound information from the same current heartbeat phase. In this way he can make optimal use of the important information contained in the IVUS images.

The IVUS images $I_1, I_2, I_3$ displayed on the monitor 12 belong to various known positions x along the vessel 2. As shown in the FIGURE, in this respect the physician is shown the respective location of the IVUS images $I_1, I_2, I_3$ for example by connecting lines on the current image $A_t$.

According to one modification or further development of the method, the processor 9 selects, among the IVUS images I(E,x) from the memory area 10, only one (or a few) which have been generated at least approximately at the current stopping location of the catheter 13. In a modification of the FIGURE, therefore, only the IVUS image $I_2$ which corresponds to the current stopping location of the catheter tip 13 would be displayed on the monitor 12. The physician then sees, next to the current fluoroscopic image $A_t$, at all times the associated vessel cross section at the location of the catheter tip. In this connection, it may be useful or necessary to carry out a weighting of the selection criteria "corresponding to the stopping location of the object" and "corresponding to the ECG phase". That is to say, depending on the settings of the user, that IVUS image which best corresponds to the current position of the catheter 13 is selected and displayed, or that IVUS image which best corresponds to the current heart phase is selected and displayed, or an IVUS image in which a weighted compromise between the abovementioned criteria is met is displayed.

Finally, it should be pointed out that the method and system described preferably also take account of the breathing phase, which is dealt with in a manner analogous to the heart phase.

The invention claimed is:

1. A method for displaying a patient's vessel and an object of interest in real time during a medical intervention in the patient, the method comprising the steps:
   a) recording and storing in a physical memory in a run-up previous to the medical intervention a sequence of intravascular ultrasound vessel cross section images of the vessel from an intravascular ultrasound pull back sequence;
   b) recording and storing in the same physical memory angiograms of the vessel obtained from an x-ray device while injecting contrast agent;
   c) indexing the ultrasound vessel cross section images and angiograms at the time of their recording by respective locations of their recording in the vessel;
   d) indexing the ultrasound vessel cross section images and angiograms at the time of their recording by respective values of a cyclic heartbeat of the patient's heart;
   e) indexing the ultrasound vessel cross section images and angiograms at the time of their recording by respective values of a cyclic breathing of the patient;
   f) detecting a current location in the vessel of the object of interest in real time during the medical intervention using an x-ray or NMR (nuclear magnetic resonance) image device to provide a current location image;
   g) detecting a current value of the cyclic heartbeat using an electrocardiogram;
   h) detecting a current value of the cyclic breathing using a breathing sensor, and recording the current values of the cyclic heartbeat and the cyclic breathing along with the current location image;
   i) selecting three or more ultrasound vessel cross section images from the sequence of stored ultrasound vessel cross section images, wherein the selected images have locations of their recording that lie within the current location image and have the same current values of the cyclic heartbeat and the cyclic breathing as the current location image; and
   j) displaying the selected ultrasound vessel cross section images concurrently with the current location image or a stored angiogram corresponding to the current location image, showing the locations of the recording in the vessel of each of the selected ultrasound vessel cross section images with reference to the current location image or stored angiogram with symbols.

2. The method of claim 1, wherein the object of interest is a catheter tip.

3. The method of claim 1, wherein the object of interest is an anatomical vessel structure of the vessel.

4. The method of claim 1, wherein the medical intervention is a catheter examination and the vessel is the patient's heart.

5. The method of claim 1, wherein the vessel is a heart vessel.

6. A RAM or hard disk storing instructions executable by a computer, the instructions operable to perform a method for displaying a patient's vessel and an object of interest in real time during a medical intervention in the patient, the method comprising the steps:
   a) recording and storing in physical memory in a run-up previous to the medical intervention a sequence of intravascular ultrasound vessel cross section images of the vessel from an intravascular ultrasound pull back sequence;
   b) recording and storing in the same physical memory angiograms of the vessel obtained from an x-ray device while injecting contrast agent;
   c) indexing the ultrasound vessel cross section images and angiograms at the time of their recording by respective locations of their recording in the vessel;
   d) indexing the ultrasound vessel cross section images and angiograms at the time of their recording by respective values of a cyclic heartbeat of the patient's heart;
   e) indexing the ultrasound vessel cross section images and angiograms at the time of their recording by respective values of a cyclic breathing of the patient;
   f) detecting a current location in the vessel of the object of interest in real time during the medical intervention using an x-ray or NMR image device to provide a current location image;
   g) detecting a current value of the cyclic heartbeat using an electrocardiogram;
   h) detecting a current value of the cyclic breathing using a breathing sensor, and recording the current values of the cyclic heartbeat and the cyclic breathing along with the current location image;
   i) selecting three or more ultrasound vessel cross section images from the sequence of stored ultrasound vessel cross section images, wherein the selected images have locations of their recording that lie within the current location image and have the same current values of the cyclic heartbeat and the cyclic breathing as the current location image; and
   j) displaying the selected ultrasound vessel cross section images concurrently with the current location image or a stored angiogram corresponding to the current location image, showing the locations of the recording in the vessel of each of the selected ultrasound vessel cross section images with reference to the current location image or stored angiogram with symbols.

7. A computer programmed to perform a method for displaying a patient's vessel and an object of interest in real time during a medical intervention in the patient, the method comprising the steps:
   a) recording and storing in physical memory in a run-up previous to the medical intervention a sequence of intravascular ultrasound vessel cross section images of the vessel from an intravascular ultrasound pull back sequence;
   b) recording and storing in the same physical memory angiograms of the vessel obtained from an x-ray device while injecting contrast agent;
   c) indexing the ultrasound vessel cross section images and angiograms at the time of their recording by respective locations of their recording in the vessel;
   d) indexing the ultrasound vessel cross section images and angiograms at the time of their recording by respective values of a cyclic heartbeat of the patient's heart;
   e) indexing the ultrasound vessel cross section images and angiograms at the time of their recording by respective values of a cyclic breathing of the patient;

f) detecting a current location in the vessel of the object of interest in real time during the medical intervention using an x-ray or NMR image device to provide a current location image;
g) detecting a current value of the cyclic heartbeat using an electrocardiogram;
h) detecting a current value of the cyclic breathing using a breathing sensor, and recording the current values of the cyclic heartbeat and the cyclic breathing along with the current location image;
i) selecting three or more ultrasound vessel cross section images from the sequence of stored ultrasound vessel cross section images, wherein the selected images have locations of their recording that lie within the current location image and have the same current values of the cyclic heartbeat and the cyclic breathing as the current location image; and
j) displaying the selected ultrasound vessel cross section images concurrently with the current location image or a stored angiogram corresponding to the current location image, showing the locations of the recording in the vessel of each of the selected ultrasound vessel cross section images with reference to the current location image or stored angiogram with symbols.

* * * * *